July 25, 1950 C. G. DUEHRSEN Plant Pat. 967
ROSE PLANT
Filed July 26, 1949
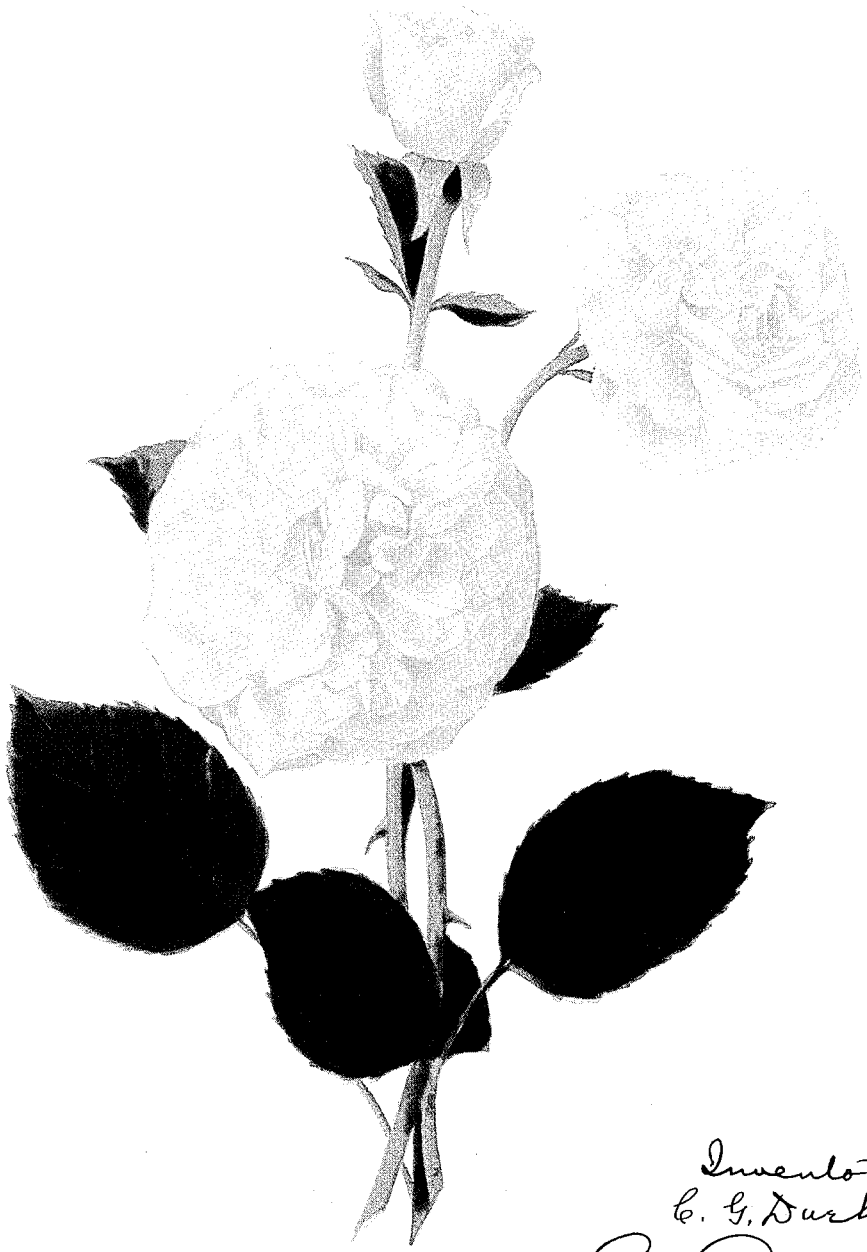
Inventor
C. G. Duehrsen
By Robert Robb
Attorneys Patented July 25, 1950

UNITED STATES PATENT OFFICE

967

ROSE PLANT

Carl G. Duehrsen, Montebello, Calif., assignor to Constance A. Elmer, trading as Elmer Roses, San Gabriel, Calif.

Application July 26, 1949, Serial No. 106,927

1 Claim. (Cl. 47—61)

This invention relates to a new and distinct variety of polyantha rose plant, resulting from a cross of an unnamed seedling and "Baby Chateau," a well-known crimson variety.

This new variety is characterized as to novelty by the attractive coloring of its flowers, a pure, clear shade of pink, and the form and arrangement of the tiny petals which are packed closely together with a suggestion of a point at the outer edge of each petal. The color of the rose is slightly deeper at its center; it shows no sense of fading to a lighter shade at the outer edge, but rather, due to its compactness, its general tonality appears to be that of its deeper toned center.

When fully open the flower resembles more nearly that of the variety "Rosenelfe" (unpatented) more than any of which I am aware, however, differing therefrom by a clearer color tone, not whitening out with age, but rather deepening in shades of pink. It differs also from "Pinocchio" (Pl. Pat. #484) in that it does not cluster in solid mass form as is the case in "Pinocchio," distinguishing from the latter because of its habit of carrying about eight flowers on one main stem, spaced from each other as though arranged for exhibition purposes. These stems are quite strong enough to carry the bloom gracefully and with the added feature of attractive disease resistant foliage, this new hybrid polyantha is most suitable for outdoor decoration as well as cut flower purposes.

Asexual reproduction of this new variety shows the foregoing characteristics come true to form and are established.

In the drawing are shown specimens of this new variety of rose and its foliage at different stages of development of the same.

This new variety was asexually reproduced at Montebello, California, by budding.

The following is a detailed description of the new variety, reference to color being in accordance with British Color Council Chart, except where indicated to have ordinary dictionary significance.

Type: Hardy; dwarf; bush; outdoor, seedling; for cut flowers and garden decoration.
Class: Polyantha.
Breeding: Seedling.
*Seed parent.*—Unnamed seedling.
*Pollen parent.*—"Baby Chateau" (unpatented).
Propagation: Holds its distinguishing characteristics through succeeding propagations.

*Flower*

Locality where grown: Montebello, California.
Flowers borne: Several, 5 to 8, to stem in flat cluster; on strong, medium-length stems.
Quantity of bloom: Abundant; outdoors.

Continuity: Continuous.
Fragrance: Moderate; Sweetbriar.
Bud:
*Peduncle.*—Short; erect; stiff; green bronze; almost smooth; few brown hairs.
*Before calyx breaks.*—Size—small. Form—flat; ovoid; with appendages on the surface of the bud; with entire, bristle-like foliaceous parts extending beyond the tip of the bud equal to one-fourth of its length.
*As calyx breaks.*—Color— Rhodamine Pink, Plate 527.
*As first petal opens.*—Size—small. Form—ovoid. Color—outside: Rhodamine Pink, Plate 527; inside: Shell Pink, Plate 516/3.
*Opening.*—Opens up well.
Bloom: Size, when fully open—small; 2¾ inches to 3 inches.
*Petalage.*—Very double; from 45 to 50 petals arranged irregularly.
*Form.*—Flat; petals remaining at first slightly rolled outward; becoming later, at maturity, tightly rolled outward.
Petals: Leathery; with inside satiny and outside satiny.
*Shape.*—Outside—round; scalloped with two notches. Inside and intermediate—oval; scalloped with two notches.
*Color.*—Colors may be modified by being tinted with other colors.

This description of a newly opened flower was made from a rose grown outdoors in the month of February, at Montebello, California:

*Color. — Outside petal* — outside surface: Dawn Pink, Plate 523; inside surface: Dawn Pink, Plate 523/3. *Intermediate petal*—outside surface: Dawn Pink, Plate 523; inside surface: Dawn Pink, Plate 523/3. *Inner petal* — outside surface: Dawn Pink, Plate 523; inside surface: Dawn Pink, Plate 423/3.

This description was made from a rose that was open for three days outdoors in the month of May, at Montebello, California:

*Color.—Outside petal* — outside surface: Dawn Pink, Plate 523; inside surface: Dawn Pink, Plate 523/3. *Inside petal*—outside surface: Dawn Pink, Plate 523; inside surface: Dawn Pink, Plate 523/3.
*General color effect.*—Newly opened flower —Dawn Pink, Plate 523/3. Three days open—French Rose, Plate 520/3.
*Behavior.*—Drop off cleanly; has experienced 18° low and 98° high with no damage.
*Flower longevity.*—On bush in garden—4 to 5 days. Cut roses grown outdoors, kept at living-room temperatures—5 to 6 days.

*Reproductive organs*

Stamens: Few; arranged regularly about pistils.
Filaments: Short; yellow; few; most without anthers.
Anthers: Small; reddish brown; all open at once.
Pollen: Sparse.
Pistils: Few.
Styles: Even; short; medium heavy; bunched.
Stigma: Red brown.
Ovaries: All enclosed in calyx.
Hips: Short; pointed with inconspicuous neck; pear-shaped or gourd-shaped; green; smooth; thin.
Sepals: Permanent; moderate length; spear-shaped.

*Plant*

Foliage: Leaves, compound of five leaflets; normally abundant; medium large; leathery; glossy.
*Leaflets.*—Oval, with apex acute; margin serrate.
*Color.*—*Mature*—upper surface—dark green; under surface—gray green. *Young*—upper surface—green bronze; under surface—gray green.
*Rachis.*—Upper side—smooth; grooved. Under side—sparsely thorny.
*Stipules.*—Medium length points, turning out at an angle of more than 45°.
*Disease.*—Resistant to mildew and blackspot.

Growth:
*Habit.*—Bushy; upright.
*Growth.*—Vigorous.
*Canes.*—Medium heavy.
*Main stems.*—Bright green. *Thorns*—several; medium length; hooked downward; with long, narrow base. *Prickles*—few; green. *Hairs*—none.
*Branches.*—Bright green. *Thorns* — few; hooked downward; with long, narrow base. *Prickles and hairs*—none.
*New shoots.*—Dull green. *Thorns*—few; short; hooked downward; with long, narrow base. *Prickles and hairs*—none.

I claim:

A new and distinct variety of hybrid polyantha rose plant substantially as herein described and illustrated, characterized as to novelty by the color and form of its flowers, the lack of fading to lighter shades at the outer edges; the compactness of the petals of the flower which give rise to apparent deepening of the color tones; its production of a large number of flowers per stem in somewhat open arrangement; strength of the flower carrying stem; and disease resistant foliage.

CARL G. DUEHRSEN.

No references cited.